United States Patent [19]

Atlas

[11] Patent Number: 4,540,002
[45] Date of Patent: Sep. 10, 1985

[54] ELECTRICAL MEASURING SYSTEM PARTICULARLY USEFUL FOR THE NON-INVASIVE EXAMINATION OF BIOLOGICAL TISSUE

[76] Inventor: Dan Atlas, Hod Hasharon, Israel, 45102

[21] Appl. No.: 429,673

[22] Filed: Sep. 30, 1982

[30] Foreign Application Priority Data

Apr. 22, 1982 [IL] Israel ........................................ 65581

[51] Int. Cl.³ .............................................. A61B 5/04
[52] U.S. Cl. ..................................................... 128/734
[58] Field of Search ................................ 128/733, 734

[56] References Cited

U.S. PATENT DOCUMENTS 3,750,649  8/1973  Severinghaus .................... 128/734 X
4,344,441  8/1982  Radke ................................... 128/733

OTHER PUBLICATIONS

'Moffitt L. R., "A Versatile and Economical Impedance Plethysmograph", Proc. 9th Ann. Rocky Mtn. Bioeng Symp. and 10th Internt'l. ISA Biomed Science, Instrument, Symp., vol. 9, Omaha Nev. USA (May 1-3, 1972).
Benabid A. L., et al., "Elect. Imped Brain Scan: Prine Prelim Res. of Simue", TIT Jour. of Life Science, vol. 8, No. 1-2.
Henderson R. P. et al., "Imped Camera for Spatially Specific Measurements of the Thorax", IEEE Trans Biomed, vol. BME 25, No. 3 5/78.

*Primary Examiner*—Kyle L. Howell
*Assistant Examiner*—Francis J. Jaworski
*Attorney, Agent, or Firm*—Benjamin J. Barish

[57] ABSTRACT

A system for measuring electrical impedance particularly of biological tissues to provide an indication of the condition of such tissue. The system comprises a source of constant-amplitude current and three pairs of electrodes, of which the first pair constitutes excitational electrodes, the second pair constitutes sensing electrodes, and the third pair constitutes focusing electrodes to focus the current flowing between the two excitation electrodes to the region occupied by the sensing electrodes. The system further includes synchronized switching means for alternately connecting the first group and the second group of electrodes to the excitation source.

7 Claims, 5 Drawing Figures

SELECTOR 26 MODES:

ABSOLUTE:
  DUAL: A, B
  DIFFERENCE: A-B or B-A

NORMALIZED:
  DIFFERENCE: $\frac{|A-B|}{A+B}$
  RATIO: $\frac{A}{A+B}$ or $\frac{B}{A+B}$ ELECTRICAL MEASURING SYSTEM PARTICULARLY USEFUL FOR THE NON-INVASIVE EXAMINATION OF BIOLOGICAL TISSUE

BACKGROUND OF THE INVENTION

The present invention relates to electrical measuring systems. The invention is particularly useful for making certain biological measurements useful in the non-invasive examination of biological tissue, and is therefore described below with respect to such applications.

One such application described below, for which the invention is eminently suitable, is the impedance measurement of sections of biological tissue, e.g., to provide an indication of the condition of such tissue. A second application, also described below, is in monitoring the muscle-tension of a subject, e.g., in measuring the jaw bite of the subject.

The impedance measurement of sections of biological tissue, by providing an indication of the condition of such tissue, allows the non-invasive monitoring of changes associated with such tissue, particularly in the subdermal concentration of fluids. For example, a wound, burn or skin graft tends to exhibit an impedance which is inversely proportional to the accumulation of biological fluids, and therefore the monitoring of the impedance of the biological tissue, particularly the dermis or deep-tissue impedance, provides a means, which is not disturbing, nor intrusive nor cumbersome to the subject, for monitoring the progress and state of the wound, burn or skin graft.

One simple system for measuring the electrical impedance of biological tissue includes a source of constant-amplitude current, a pair of electrodes applied across the portion of the tissue under examination, and means for measuring the voltage drop across the pair of electrodes, thereby providing a measurement of the impedance in the respective portion of the biological tissue under examination. However, such a "two-electrode" system cannot distinguish between the dermis or deep-tissue impedance, which is of the primary interest, from either the contact impedance or the epidermis impedance, and therefore such "two-electrode" systems are not very sensitive. Three-electrode systems and four-electrode systems have been devised to increase the sensitivity of the system in the above respects, but these too are still not as sensitive as would be required for effectively monitoring the condition of the tissue by observing its change in impedance.

For example, a four-electrode system includes a first pair, constituting excitational electrodes, adapted to be applied in spaced relationship to each other to the tissue under examination and to be connected to the source of constant-amplitude current; and a second pair, constituting sensing electrodes, adapted to be applied to the subject under examination in alignment with, and in the space between, the excitation electrodes and in spaced relationship to each other. Since a constant current is applied to the tissue under examination, the voltage measured by the sensing electrodes provides a measurement of the impedance between them, and thereby, of the impedance in the tissue under examination. Thus, the measurement produced by the four-electrode system (i.e., the voltage drop between the sensing electrodes) does not include either the contact-impedance or the epidermis impedance measurements. However, while such a four-electrode system provides an output closer to the actual dermis or deep-tissue impedance than the mentioned two-electrode system (or three-electrode system), it too is not exact, as will be explained more fully below.

One object of the present invention is to provide an electrical measuring system which, when used for measuring the impedance of biological tissue, provides an even more accurate measurement, than the four-electrode system, of the impedance of primary interest, namely the dermis or deep-tissue impedance.

Certain features of the electrical measuring system of the present invention may advantageously be used in making and evaluating other electrical measurements, such as in monitoring the muscle-tension of the subject.

Accordingly, another object of the present invention is to provide an electrical measuring system which may be used in measuring not only electrical impedance but also muscle-tension, temperature, or other conditions, in a manner so as to more readily facilitate, to the observer, an evaluation of the significance of such measurements.

BRIEF SUMMARY OF THE INVENTION

According to one aspect of the present invention, there is provided a system for measuring the electrical impedance of a subject under examination, which system is particularly useful for the non-invasive examination of biological tissue, comprising a source of constant-amplitude current and a group of electrodes including a first pair, constituting excitational electrodes, adapted to be applied in spaced relationship to each other to the subject under examination and to be connected to said current source, and a second pair, constituting sensing electrodes, adapted to be applied to the subject under examination in alignment with, and in the space between, said excitational electrodes and in spaced relationship to each other so as to measure the impedance of said subject under examination by measuring the voltage drop between said sensing electrodes; characterized in that said group of electrodes further includes a third pair, constituting focusing electrodes, adapted to be applied to the subject under examination such as to focus the current flowing between the two excitation electrodes to the region occupied by said sensing electrodes, said focusing electrodes being planar electrodes and adapted to be applied to the subject under examination in alignment with, and on opposite sides of, one of the excitational electrodes transversely of the line between the two excitational electrodes.

Such an arrangement, which can be called a "hexapolar" electrode system, produces a much more accurate measurement of the dermal or deep-tissue impedance than any of the above-mentioned two, three, or four-electrode systems.

More particularly, in the described preferred embodiment, the focusing electrodes are connected to one excitational electrode such that the potential of both focusing electrodes follows that of said one excitational electrode.

According to a still further feature in the described preferred embodiment, the source of constant-amplitude current is an AC source having a substantially "zero" DC output voltage; this enables the accommodation of a large contact impedance without saturation.

According to a still further feature in the described embodiment, all the electrodes are substantially planar electrodes and are applied in a substantially common plane on the subject under examination.

According to another important aspect of the invention, the system further includes a second group of electrodes corresponding to said first-mentioned group of electrodes but adapted to be applied to another portion of the subject under examination to serve as a reference with respect thereto.

Thus, one group of electrodes may be used for monitoring the traumatized area under examination, while the other group of electrodes may be used to enable a healthy site, on the same subject and under the same ambient conditions, to serve as a dynamic, individualized reference for evaluating the measurements made by the first group of electrodes.

According to a further aspect of the invention, there is provided a system particularly useful for the non-invasive examination of biological tissue, comprising a first group of electrodes adapted to be applied to one portion of the subject under examination; a second group of electrodes, corresponding to those of said first group, and adapted to be applied to another portion of the subject under examination to serve as a reference with respect thereto; and synchronized switching means for alternately connecting said first group of electrodes to an excitation source while disconnecting said first group of electrodes therefrom.

According to a still further aspect of the invention, there is provided an electrical measuring system particularly useful for the non-invasive examination of biological tissues, comprising first sensor means adapted to be applied to one portion of the subject under examination for sensing a condition thereof; second sensor means adapted to be applied to another portion of the subject under examination to serve as a reference with respect thereto; first and second display means; a mode selector; and mode selector circuit means controlled by said mode selector so as to display the measurement of said first sensor means, referred to as measurement "A", and the measurement of said second sensor means, referred to as measurement "B", according to any one of a plurality of operational modes as selected by said mode selector; said mode selector circuit means including means enabling said mode selector to select: (1) an "absolute dual" mode, wherein said first display means displays measurement "A", and said second display means displays measurement "B"; (2) an "absolute difference" mode, wherein only one of said display means, namely that for the larger of the measurements "A" and "B", displays the difference between measurements "A" and "B"; or (3) a "normalized ratio" mode, wherein the display means for the larger of measurements "A" and "B" displays the larger of measurements "A" or "B" divided by the sum of measurements "A" and "B".

Two embodiments of the latter aspect of the invention are described below, one embodiment for measuring the impedance of biological tissue, and the other embodiment for measuring muscle-tension. In both described embodiments, the mode selector circuit means enables mode selectors to further select: (4) a "normalized difference" mode, wherein the display means for the larger of measurements "A" and "B" displays the difference between measurements "A" and "B" divided by the sum of measurements "A" and "B".

This capability of the described systems further aids the user in evaluating the results of the measurements made with respect to the individual case, since selecting one of the normalized modes enables the introduction of a more meaningful mathematical weighing factor of one channel against the average baseline of both channels.

Further features and advantages of the invention will be apparent from the description below.

BRIEF DESCRIPTION OF THE DRAWINGS

The invention is herein described, by way of example only, with reference to the accompanying drawings, wherein:

FIGS. 3 and 4 illustrate one implementation of an impedance measuring system according to FIG. 2, FIG. 3 illustrating the control panel of such an implementation, and FIG. 4 illustrating the overall circuit of such an implementation; and FIG. 5 illustrates another implementation of the invention as embodied in a muscle-tension monitor, such as may be used in measuring the jaw bite of a subject.

THE PRIOR ART (FIG. 1)

Figure 1:
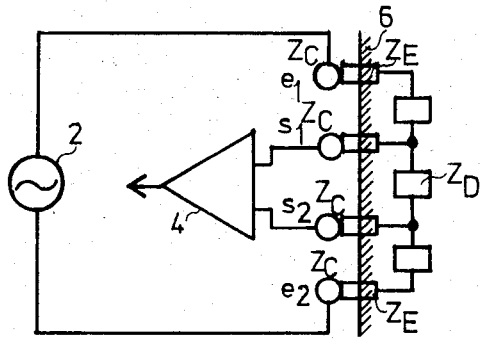
FIG. 1 illustrates a known (prior art) four-electrode system which will be described below in order to aid in understanding the novel aspects of the present invention and the advantages obtainable by it.

The four-electrode impedance measuring system illustrated in FIG. 1, known in the prior art, is a single-channel system comprising two excitation electrodes $e_1$, $e_2$ adapted to be connected to a current source 2 of constant-amplitude current; and a pair of sensing electrodes $s_1$, $s_2$ adapted to be connected to an output circuit, schematically designated 4. The excitation electrodes $e_1$, $e_2$ are applied at spaced locations to the skin 6 under examination as illustrated in FIG. 1, with the sensing electrodes $s_1$, $s_2$ applied to the skin in alignment with, and in the space between, the excitation electrodes, and in spaced relationship to each other. It will thus be seen that since a constant current flows through the skin 6 and the underlying tissue, the voltage sensed by the two sensing electrodes $s_1$, $s_2$ will be a measurement of the dermal or deep-tissue impedance between the two sensing electrodes, as indicated by the equivalent impedance designated $Z_D$ in FIG. 1, and will not include measurements of either the contact impedances $Z_C$ or the epidermal impedance $Z_E$. Once the dermal impedance $Z_D$ for a known area is measured, the dermal impedance for any larger or smaller area can be determined, as it is assumed that the impedance remains uniform over the area of interest.

Thus, the illustrated four-electrode system does not include either the contact impedance or the epidermal impedance in its output. However, its output is still not a true measurement of the dermal impedance alone since fringe currents between the two excitation electrodes $e_1$, $e_2$, as shown by the broken line in FIG. 1, will flow without being detected by the sensing electrodes $s_1$, $s_2$. This is a very serious drawback in the known four-electrode system. Another drawback in the known four-electrode system illustrated in FIG. 1 is that no account is taken for variations in the operating conditions or in the subject itself when the measurements are taken, for example, variations in ambient temperature, seasons, electrode size and spacing, body temperature, body perspiration, etc., any of which variations can significantly affect the output results.

DESCRIPTION OF PREFERRED EMBODIMENTS

Figure 2:
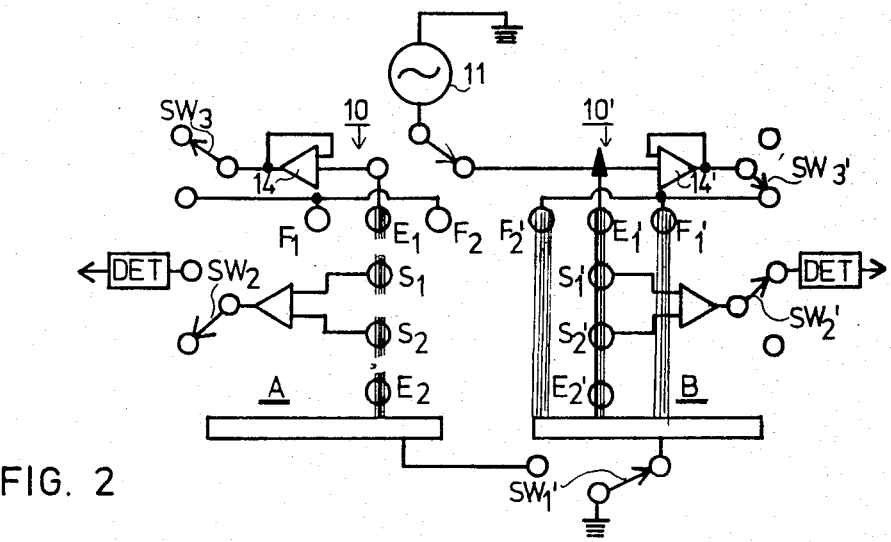
FIG. 2 is a schematic diagram illustrating the main elements of a six-electrode, two-channel system constructed in accordance with the present invention.

The Six-Electrode, Two-Channel System of FIG. 2

The foregoing drawbacks in the known four-electrode single-channel system illustrated in FIG. 1 are substantially lessened or completely eliminated in the two-channel hexapolar-electrode system illustrated in FIG. 2. In the FIG. 2 system, the two channels are labelled A and B, respectively, each channel including a like group of six electrodes, 10 and 10', respectively. Thus, with respect to Channel A, it will be seen that this channel includes a group 10 of electrodes comprising the same four electrodes as in the four-electrode system illustrated in FIG. 1, namely the two excitation electrodes $E_1$, $E_2$, and the two sensing electrodes $S_1$, $S_2$. However, the illustrated six-electrode system further includes an additional pair of electrodes, hereinafter referred to as focusing electrodes $F_1$, $F_2$. The two focusing electrodes $F_1$, $F_2$, as shown in FIG. 2, are adapted to be applied to the subject under examination on opposite sides of one of the excitation electrodes ($E_1$) in a line extending through it and transversely of the line between it and the second excitation electrode $E_2$. As will be described below, the two focusing electrodes $F_1$, $F_2$ are connected to the excitation electrode $E_1$ in a manner such that the potential of both focusing electrodes follows that of the excitation electrode $E_1$.

The circuit illustrated in FIG. 2 comprises a source of excitation current 11 providing constant-amplitude current to the two excitation electrodes $E_1$, $E_2$. The sensing electrodes $S_1$, $S_2$ are connected to an output circuit 12 outputting the measurement "A" for Channel A. In Channel A, excitation electrode $E_1$ is connected to one input terminal of a high-impedance differential amplifier 14, the output terminal of which is connected, via a synchronizing switching device described later, to the two focusing electrodes $F_1$, $F_2$. The output of amplifier 14 is also fed back to a second input terminal of the same amplifier, such that the amplifier output voltage, and thereby the voltage applied to the focusing electrodes $F_1$, $F_2$, follows the amplifier input voltage and thereby the voltage applied to the excitation electrode $E_1$.

Thus, the potential of the focusing electrodes $F_1$, $F_2$, on opposite sides of the excitation electrode $E_1$, follows that of the excitation electrode $E_1$. The focusing electrodes are thus effective to "focus" the current flowing between the two excitation electrodes $E_1$, $E_2$, to the region occupied by the two sensing electrodes $S_1$, $S_2$. That is to say, since the fringe regions on the opposite sides of the excitation electrode $E_1$ are at the same potential as that electrode, and since there is no current flow between points at the same potential, there will be no, or very little, current flow in the fringe regions between the two excitation electrodes $E_1$, $E_2$. Accordingly, all, or virtually all, the current between the two excitation electrodes will flow in the space occupied by the two sensing electrodes $S_1$, $S_2$. The voltage detected by the two sensing electrodes $S_1$, $S_2$, during this flow of constant current between the two excitation electrodes $E_1$, $E_2$, will therefore be a truer measurement, compared to the four-electrode system illustrated in FIG. 1, of the actual dermal or deep-tissue impedance between the two sensing electrodes $S_1$, $S_2$.

Channel B in the system illustrated in FIG. 2 includes a second group 10' comprising the identical electrodes as described above with respect to group 10 for Channel A. Thus, the electrodes 10 of Channel A are to be applied to the traumatized site under examination, and the electrodes 10' of Channel B are to be applied to a healthy site of the same subject, so as to be used as a reference for Channel A in order to take into account variations applicable to that particular patient or to the particular conditions under which the examination is being made.

Thus, the six-electrode system 10' of Channel B includes the corresponding three pairs of electrodes as in electrode system 10 for Channel A, namely the pair of excitation electrodes $E_1'$, $E_2'$, the pair of sensing electrodes $S_1'$, $S_2'$, and the pair of focusing electrodes $F_1'$, $F_2'$. The excitation electrodes $E_1'$, $E_2'$ are connected to the same source of excitation current 11 as the electrodes in Channel A; the sensing electrodes $S_1'$, $S_2'$ are connected to the output circuit 12' of Channel B to output the measurement "B"; and the focusing electrodes $F_1'$, $F_2'$ are connected via differential amplifier 14' to excitation electrodes $E_1'$ so as to follow the potential of that electrode, all in the same manner as described above with reference to Channel A.

The system illustrated in FIG. 2 further includes means for alternately enabling Channel A while disabling Channel B, and then enabling Channel B while disabling Channel A. This is performed by the synchronous switching circuit schematically illustrated in FIG. 2 as including: switches $SW_1$, $SW_1'$, which alternately steer the excitation current 11 first to Channel A and then to Channel B; switches $SW_2$, $SW_2'$, which alternately connect the output circuits 12, 12' to their respective output channels A and B; and switches $SW_3$, $SW_3'$, which alternately connect the focusing electrodes of each channel to their respective excitation electrodes.

It will thus be seen that the six-electrode, two-channel system illustrated in FIG. 2 provides a number of important advantages over the known four-electrode, single-channel system illustrated in FIG. 1, including an increased sensitivity in the measurement of the dermal or deep-tissue impedance, and a reference for the evaluation of the measured impedance with respect to variations in the ambient conditions or the condition of the patient when the measurements are actually taken.

Figure 3:
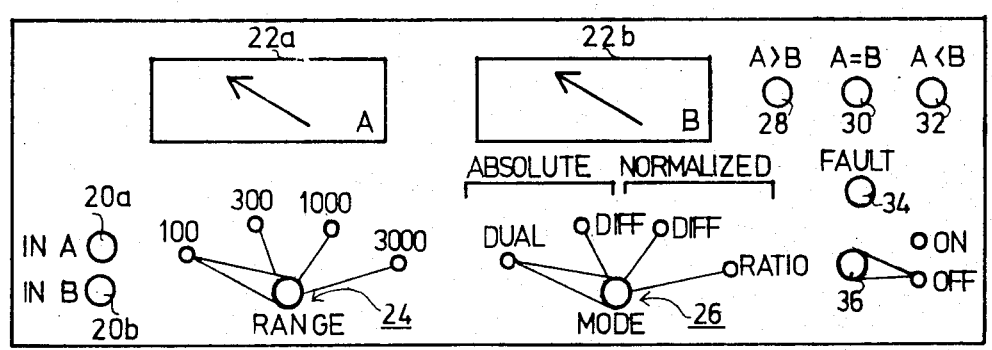

Implementation Illustrated in FIGS. 3 and 4

FIGS. 3 and 4 illustrate a preferred implementation of an impedance measurement system constructed as described above with respect to FIG. 2. FIG. 3 illustrates the control panel of this preferred implementation, and FIG. 4 illustrates the circuit included in this implementation.

With reference first to FIG. 3, the control panel, therein designated CP, has a pair of input terminals 20a, 20b, for inputting the Channel A and Channel B measurements from the electrode system illustrated in FIG. 2. In addition, control panel CP includes two display devices, in the form of analog meters 22a, 22b, which display the measured information, or other data processed from it, as will be described more particularly below. Control panel CP further includes a range selector 24 for selecting the range of impedance measurement, and a mode selector 26 for selecting one of several modes of operation of the instrument as will also be described more particularly below. Further provided on the control panel CP illustrated in FIG. 3 are three indicator lamps, namely: lamp 28, for indicating when the measurement of Channel A is greater than that of Channel B; lamp 30, for indicating when the measurement of Channel A is equal to that of Channel B; and lamp 32, for indicating when the measurement of Channel B is greater than that of Channel A. The significance of these indications is also more fully described below. Finally, control panel CP includes a fault indicator lamp 34, and an ON-OFF switch 36.

The mode selector 26 in control panel CP illustrated in FIG. 3 may be used for selecting any one of four modes of operation of the instrument, as follows: (1) an "absolute dual" mode, in which meter 22a displays measurement "A" outputted from Channel A of FIG. 2, and meter 22b displays measurement "B" outputted from Channel B of FIG. 2; (2) an "absolute difference" mode, in which only one meter displays an output, namely that meter for the larger of the measurements of "A" and "B", the display by that meter being the difference between measurements "A" and "B"; (3) a "normalized difference" mode, wherein one of the two meters 22a, 22b, namely, the one for the larger of measurements "A" and "B", displays the difference between measurements "A" and "B" divided by the sum of measurements "A" and "B"; and (4) a "normalized ratio" mode, wherein the meter for the larger of the two measurements "A" and "B" displays the larger of the two measurements divided by the sum of the two measurements. In all four modes, one of the indicator lamps 28, 30, 32 will also be energized to indicate whether measurement "A" is greater than, equal to, or less than, measurement "B".

It has been found that such a mode selector arrangement greatly facilitates the evaluation by the user of the significance of the measurements. Thus, by selecting the "absolute dual" mode, the user is readily apprised of the absolute measurements of "A" and "B". However, in many cases the relative values are of more immediate interest. For example, if the impedance at the wound is rapidly decreasing, as compared to the reference site, this may indicate a condition at the wound causing a rapid inflammation or accumulation of liquid. This will be clearly indicated, when mode selector 26 is in position (2) above, by meter 22b becoming active to display the difference between measurement "B" and measurement "A", while indicator lamp 32 is energized to show that measurement "A" is less than measurement "B".

On the other hand, if the impedance at the wound site starts to increase, this may indicate a drying-out of the dressing at the wound site, and would be indicated by meter 22a becoming active and indicator lamp 28 becoming energized.

The same changes in condition will be indicated when the mode selector 26 is placed in either of the "normalized " mode positions (3) or (4), except that the value displayed by the meters 22a or 22b, corresponding to that for the larger of the two measurements "A" and "B", will be either the difference between the two measurements divided by the sum of the two measurements (position 3), or the actual larger measurement ("A" or "B") divided by the sum of the two measurements (position 4). As indicated earlier, such a "normalizing" process gives a more meaningful mathematical weighing factor of one channel against the average baseline of both channels, thereby aiding the observer in evaluating the significance of the measurements displayed.

With reference to the block diagram illustrated in FIG. 4, the instrument comprises an isolated low voltage supply 50, such as a battery, providing output voltages of +6 volts, +12 volts and −6 volts. The instrument further includes an oscillator circuit 52 providing an output of 50 KHz, and a variable attenuator 54 controlled by the range knob 24 in FIG. 3, to select full-scale impedance measurements of 100, 300, 1000 or 3000 Ohms. The AC voltage from source 52, after the appropriate range is selected by circuit 54, is converted by a voltage-to-current converter 56 to a current of constant amplitude, which is applied to the excitation electrodes $E_1$, $E_1'$, via the switches $SW_1$, $SW_1'$. The output of the constant-amplitude current source 56 is automatically balanced to "zero" DC voltage output by circuit 58, which is desirable in order to accommodate large contact impedance without saturation, as indicated earlier.

As one example, the full-scale voltage across the tissue between the sensing electrodes could be about 0.4 volts. Thus, if a full-scale impedance measurement of 100 Ohms is selected, this would produce a current of 4 milliamps through the tissue, which current would be correspondingly reduced by a selection of a larger full-scale impedance measurement.

The system illustrated in FIG. 4 further includes a 100 Hz multivibrator 60 whose output controls the switches $SW_1$, $SW_1'$, as well as the other switches operating in synchronism therewith for alternately enabling and disabling the two Channels A and B as described with reference to FIG. 2. An over-voltage fault detector 62 is connected to the output of the constant-current supply source 56 to monitor the output voltage applied to the patient and thereby to ensure that an excessive voltage is not applied; if an excessive voltage is detected, the voltage source 52, as well as the multivibrator 60, are both inhibited, and in addition, the fault lamp 34 on the control panel is energized.

The focusing electrodes $F_1$, $F_2$, $F_1'$ and $F_2'$, in the two Channels A and B, respectively, of FIG. 2, are alternately connected to their respective bootstrapping circuits 14, 14' by the switches $SW_3$, $SW_3'$ controlled by multivibrator 60 in synchronism with switches $SW_1$, $SW_1'$. The voltages detected by the sensing electrodes in the two Channels A and B are fed via differential amplifiers 63, 63', and filters 64 and 64' to the input terminals A and B in the control panel of FIG. 3 via the synchronous detectors, namely switches $SW_2$, $SW_2'$, controlled by multivibrator 60 in synchronism with the other described switches.

The illustrated system further includes a panel select logic 70 controlled by the mode selector knob 26 so as to select one of the four different modes of operation as described above with respect to FIG. 3, and as shown by the logic circuit including logic blocks 72, 74, 76, 78, within a DC analog processor portion 80 of the instrument. The latter portion of the instrument further includes meter controls 82 and meter logic 84 having outputs to the two meters 22a, 22b illustrated in the control panel of FIG. 3. The DC analog processor 80 portion of the instrument in FIG. 4 further includes outputs to the indicator lamps 28, 30, 32 for indicating, respectively, whether measurement "A" is greater than "B", equal to "B", or less than "B".

The measurements of Channel A and Channel B may also be applied to a circuit 86 for providing optically isolated monitor outputs, such as to graphic recording equipment (not shown).

It will be seen that the DC analog processor 80, in the instrument illustrated in FIG. 4, permits the outputs of the two channels A and B, representing, respectively, the impedance measurements in the traumatized site and in the reference site of the same subject, to be processed according to a selected mode in order to provide either absolute values or normalized values of the measurements "A" and "B".

The techniques described above for increasing the sensitivity of the dermal or deep-tissue impedance measurement by the use of the six or hexapolar-electrode system, and by the use of the synchronizingly switched two-channel arrangement at the traumatized site and at a healthy site on the same patient, provide advantages which are important in non-invasive monitoring of minute impedance variations in biological tissue, such as in assessing skin graft rejection and skin flap viability, in evaluating the efficacy of laser versus scalpel surgical techniques in terms of healing rates, and in determining the need for, and the efficacy of, various drugs to contain inflammation. In addition, the synchronous switching arrangement for alternately enabling and disabling the two channels permit both channels to enjoy the same excitation conditions via a single frequency source, while provided transformerless and total interchannel isolation, thereby avoiding many of the disadvantages, such as cross-talk between channels, in using two frequency souces.

Implementation Illustrated in FIG. 5

FIG. 5 illustrates another implementation of the invention as embodied in a muscle-tension monitor, for example in making jaw bite face measurements of a subject. Thus, it includes a first group of electrodes, generally designated 110, included in a muscle-tension sensor MTS applied to one site of the patient, and a second group of electrodes 110' including another muscle-tension sensor MTS' applied to a second site to serve as a reference. The output of electrode group 110 is fed to a first Channel A including a pre-amplifier 162, a filter/amplifier 164, and an integrator 166; and the output from electrode group 110' is fed to a similar second Channel B, including a pre-amplifier 162', a filter/amplifier 164', and an integrator 166'. The outputs of the two Channels A and B are fed into a DC analog processor 180 of the same construction as processor 80 in FIG. 4; i.e., processor 180 includes a panel select logic circuit 170 controlled by a mode selector knob 126 so as to select one of the four different modes of operation as described above with respect to FIGS. 3 and 4 and as shown by the logic circuit within processor 180, including logic blocks 172, 174, 176 and 178. Processor 180 further includes meter controls 182 and meter logic 184 having outputs to the two meters 122a, 122b, and to the three indicator lamps 128, 130 and 132, all controlled as described above with respect to FIGS. 3 and 4. The measurements of Channels A and B may also be applied to an output monitor circuit 186, e.g., for graphic recording equipment, as also included in the processor of FIG. 4.

The instrument illustrated in FIG. 5 will thus operate as described above with respect to FIGS. 3 and 4, except that instead of providing a measurement of the impedance of the biological tissue at a traumatized site occupied by one group of electrodes, as compared to a second, healthy site occupied by the second group of electrodes, in the system of FIG. 5 the measurements will be of the muscle-tension sensed by the electrode group 110 at one site of the patient, as compared to that sensed by electrode group 110' at a second site of the patient. In the muscle-tension monitor of FIG. 5, no excitation source is needed, since the electrode sensors MTS, MTS' themselves are of known voltage generating type which generate voltages corresponding to the muscle-tension to be sensed. However, by the use of the mode selector 126 in FIG. 5, the user can select the manner of displaying the muscle-tension measurements of Channels A and B, either according to the two absolute modes or the two normalized modes, to enable the user to more readily evaluate the significance of the measurements.

It will be appreciated that many variations and other applications of the invention may be made. Thus, instead of using a DC analog processor, a digital processor, such as a microprocessor, could be used, and the measurements themselves could be displayed either in digital and/or analog form. Further, the impedance measuring system illustrated in FIGS. 2-4 could include, or be used with, other condition sensors, such as temperature sensors, in order to provide a more accurate indication of the actual state of the biological tissue being examined. Still further, the system, particularly the processor portion including the mode selector arrangement, could be used with still other condition sensors than the impedance and muscle-tension sensors described above, for example, temperature sensors.

Many other variations, modifications and applications of the invention will be apparent.

What is claimed is:

1. A system particularly useful for the non-invasive examination of biological tissue comprising a first group of electrodes adapted to be applied to one portion of the subject under examination; a second group of electrodes corresponding to those of said first group, and adopted to be applied to another portion of the subject under examination to serve as a reference with respect thereto, each said group, comprising:

a first pair of electrodes, constituting excitational electrodes, adapted to be applied to the respective portion of the subject under examination in spaced relationship to each other and to be connected to a source of constant-amplitude current;

a second pair of electrodes, constituting sensing electrodes, adapted to be applied to the respective portion of the subject under examination in alignment with, and in the space between, the respective first pair of excitational electrodes, and in spaced relationship to each other, so as to measure the impedance of the respective portion of the subject under examination by measuring the voltage drop between said sensing electrodes;

a third pair of electrodes, constituting focusing electrodes, adapted to be applied to the respective portion of the subject under examination in alignment with, and on opposite sides of, one of the respective excitational electrodes, transversely of the line between the respective two excitational electrodes, and connected to said one excitational electrode such that the potential of the focusing electrodes follows that of the respective one excitational electrode;

and synchronized switching means for alternatively connecting said first pair of electrodes to an excitation source while disconnecting said second pair therefrom, and then connecting said second pair of electrodes to said excitation source while disconnecting said first pair of electrodes therefrom.

2. The system according to claim 1, wherein said mode-selector circuit means includes further means enabling said mode selector to further select:

a "normalized ratio" mode, wherein the display means for the larger of measurements "A" and "B" displays the larger of measurements "A" or "B" divided by the sum of measurements "A" and "B".

3. The system according to claim 1, wherein said mode-selector circuit means includes further means enabling said mode selector to further select a "normalized difference" mode, wherein the display means for the larger of measurements "A" and "B" displays the difference between measurements "A" and "B" divided by the sum of measurements "A" and "B".

4. An electrical measuring system particularly useful for the non-invasive examination of biological tissues, comprising:
   first sensor means adapted to be applied to one portion of the subject under examination for sensing a condition thereof;
   second sensor means adapted to be applied to another portion of the subject under examination to serve as a reference with respect thereto;
   first and second display means;
   a mode selector;
   and mode selector circuit means controlled by said mode selector so as to display the measurement of said first sensor means, referred to as measurement "A", and the measurement of said second sensor means, referred to as measurement "B", according to any one of a plurality of operational modes as selected by said mode selector; said mode selector circuit means including means enabling said mode selector to select:
   (1) an "absolute dual" mode, wherein said first display means displays measurement "A", and said second display means displays measurement "B";
   (2) an "absolute difference" mode, wherein only one of said display means, namely that for the larger of the measurements "A" and "B", displays the difference between measurements "A" and "B"; or
   (3) a "normalized ratio" mode, wherein the display means for the larger of measurements "A" and "B" displays the larger of measurements "A" or "B" divided by the sum of measurements "A" and "B".

5. The system according to claim 4, wherein said mode selector circuit means includes further means enabling said mode selector to further select:
   (4) a "normalized difference" mode, wherein the display means for the larger of measurements "A" and "B" displays the difference between measurements "A" and "B" divided by the sum of measurements "A" and "B".

6. The system according to claim 4, wherein said first and second sensor means comprises a first and a second group of electrodes each adapted to measure the impedance of the respective portion of the subject under examination.

7. The system according to claim 4, wherein said first and second sensor means comprises muscle-tension electrodes adapted to measure the muscle-tension of the respective portion of the subject under examination.

* * * * *